United States Patent [19]
DeRossett et al.

[11] Patent Number: 4,710,186
[45] Date of Patent: Dec. 1, 1987

[54] CLEAN AND DRY APPEARANCE FACING

[75] Inventors: Edmund Z. DeRossett, Mercerville; Thomas J. Luceri, Little Ferry, both of N.J.

[73] Assignee: Personal Products Company, Milltown, N.J.

[21] Appl. No.: 632,753

[22] Filed: Jul. 20, 1984

[51] Int. Cl.$^4$ ............................................. A61F 13/16
[52] U.S. Cl. .................................... 604/383; 604/375
[58] Field of Search .............. 604/383, 384, 367, 366, 604/370, 369, 375, 372, 380, 378

[56] References Cited

U.S. PATENT DOCUMENTS

| | | | |
|---|---|---|---|
| 3,971,381 | 7/1976 | Gibson | 604/378 |
| 4,135,021 | 1/1979 | Patchell et al. | 604/369 |
| 4,323,069 | 4/1982 | Alev et al. | 604/372 |
| 4,333,979 | 6/1982 | Sciaraffa et al. | 604/380 |
| 4,396,671 | 8/1983 | Wanka et al. | 428/513 |

Primary Examiner—John D. Yasko

[57] ABSTRACT

A facing is provided for a body fluid absorbent product which facing is not only substantially nonwettable and pervious to body fluid, but which also enhances the clean and dry appearance of the product after it has absorbed body fluids. The facing comprises a polyolefin having an open area of from about 1.3 to about 35 percent of the total area intended for the passage of body fluids and having incorporated therein a sufficient quantity of opacifying agent so as to have the sheet exhibit a brightness of at least 45 percent.

7 Claims, 7 Drawing Figures

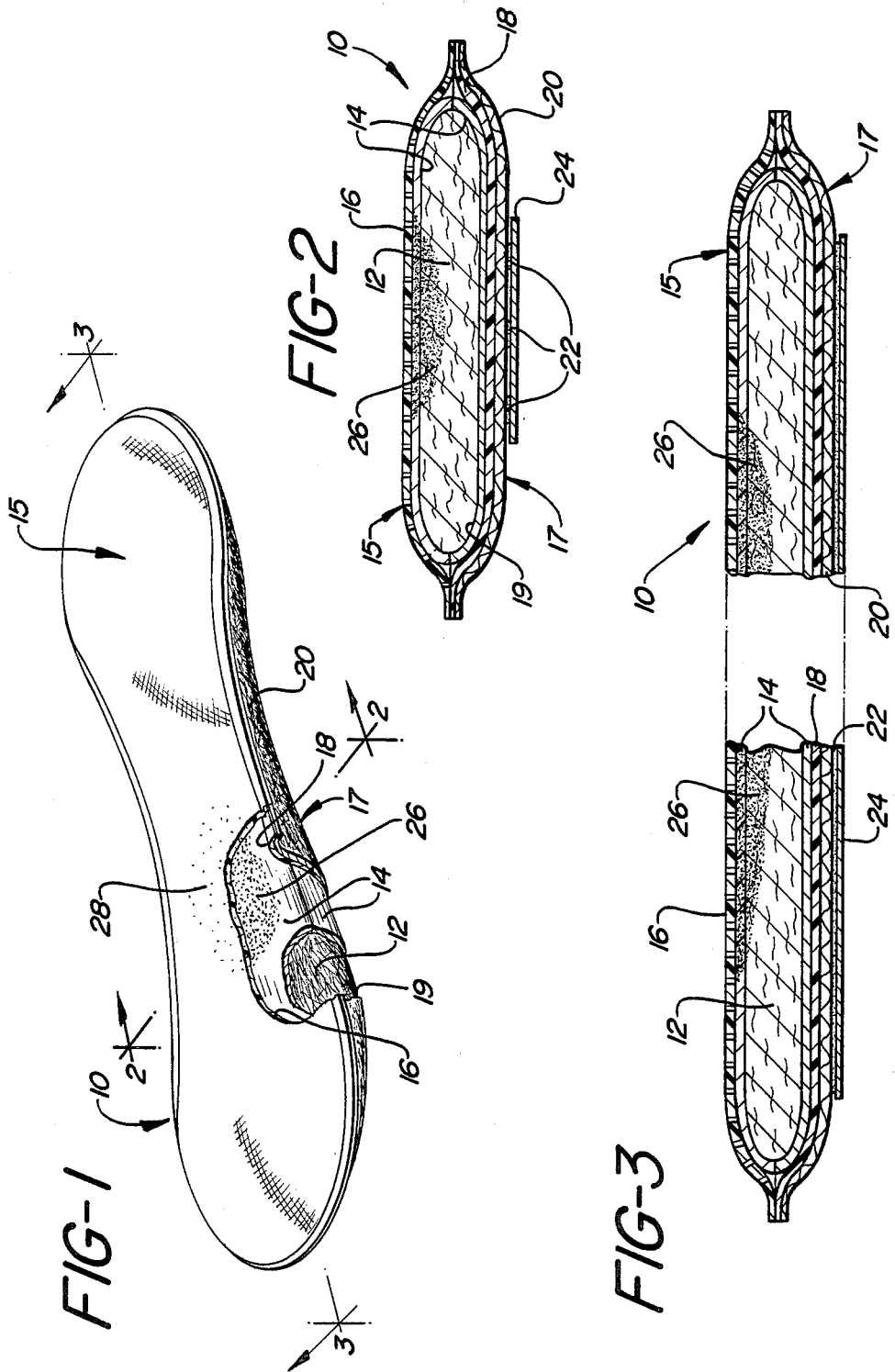

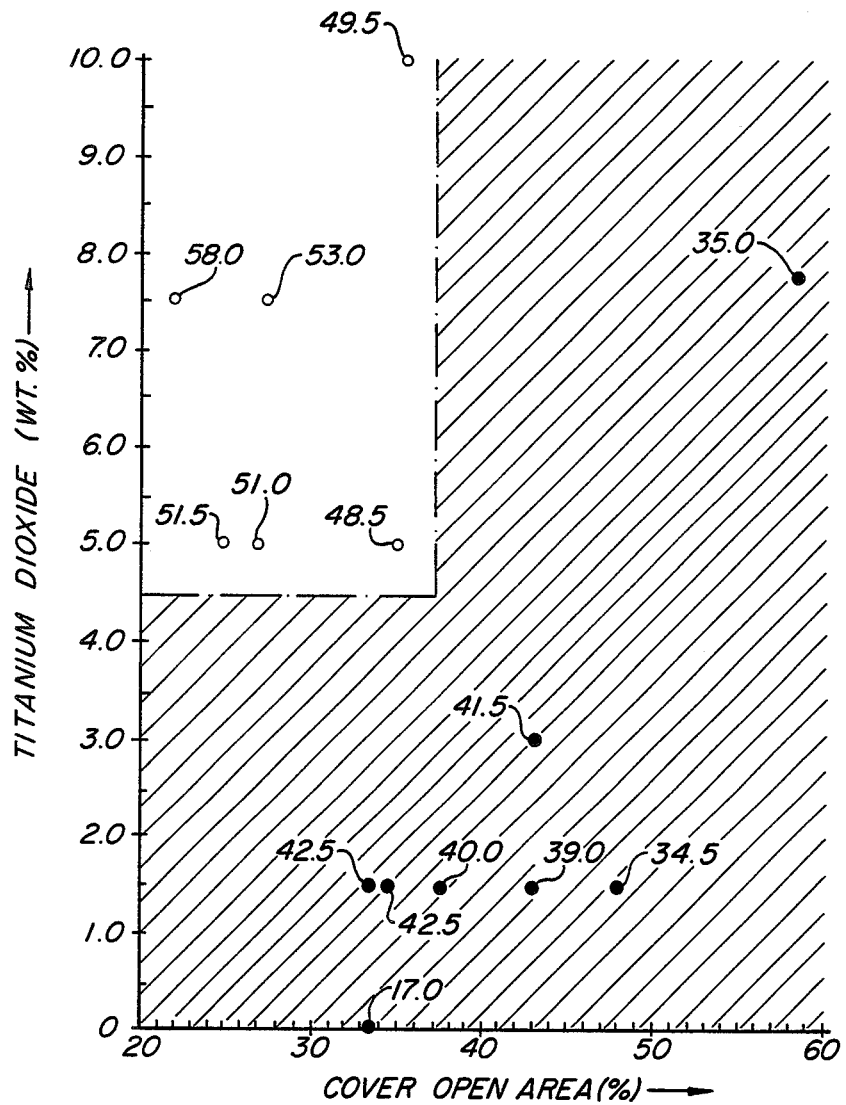

CLEAN AND DRY APPEARANCE FACING

BACKGROUND OF THE INVENTION

This invention relates to facing materials for products for absorbing body exudate and in particular, relates to facing materials for sanitary napkins whereby, after the napkin has absorbed body fluid, the facing material presents a relatively clean and dry appearance.

Absorbent products for absorbing body exudate and sanitary napkins in particular all generally comprise a body facing side, for application against the body and through which body exudate will flow; an absorbent core, for absorbing and retaining such body fluid; and a garment facing side, generally worn against the inside crotch portion of an undergarment. Usually the body facing side of the napkin comprises a sheet of body fluid pervious facing material and the garment facing side of the napkin comprises a body fluid barrier material. In some cases the sheet of which the body facing material is comprised extends completely around the product and overlies the barrier material.

Recently sheet materials for the body fluid pervious facings have been selected not only to be pervious to body fluid, but also not wettable by such fluid i.e., hydrophobic. Such hydrophobic facing materials have several well known advantages in that they remain relatively dry and hence are more comfortable in use. Additionally, by not wetting, they remain free of stain on their exterior surface. Accordingly, the art is now replete with suggestion for utilizing hydrophobic facings in body fluid absorbent products. For example in U.S. Pat. Nos. 3,695,269; 4,041,951; and 4,391,869; it has been suggested that nonwoven fabrics comprised of hydrophobic fibers be employed as the facing on absorbent products. In U.S. Pat. Nos. 2,992,644; 3,814,101; and 4,324,246; it is suggested that the facing comprise a continuous sheet of hydrophobic polymeric material, rendered permeable to body fluid by being provided with apertures.

While in the main, such hydrophobic facing materials have performed their function of allowing for the passage of body fluid therethrough without staining or wetting, it has been discovered that the user is still left with the uncomfortable perception that the facing is stained. This somewhat anomalous situation appears to be a result of the fact that notwithstanding the nonwetting, nonstaining properties of the materials from which the facing is made, the absorbent material underlying the facing clearly is stained, as it must be to function, and the stains on these underlying surfaces are visible to the user through the facing. This situation is particularly aggravated in the case of sanitary napkins wherein the stain is dark colored and is highly visible through the heretofore suggested facing materials.

Accordingly, there is a need for providing a facing material which not only can perform the desirable functions of allowing body fluid to be transmitted to the absorbent core of the product without wetting or staining the facing, but will also give the appearance of being clean and dry, thus providing the user with peace of mind.

SUMMARY OF THE INVENTION

In accordance with the teachings of this invention, a facing is provided for a product for absorbing body fluids which facing is not only substantially nonwettable and pervious but which also greatly enhances the clean and dry appearance of the product after it has absorbed such body fluids.

Specifically, the facing of this invention comprises a continuous sheet comprising a polyolefin selected from the group consisting of polyethylene, polypropylene and copolymers thereof. Incorporated into this polymeric material is a sufficient quantity of opacifying agent to have the sheet exhibit a brightness (as hereinafter defined) of at least 45%. Specifically, this may be accomplished by incorporating into the sheet from about 5 to about 12% by weight of titanium dioxide or another equivalent opacifying agent. The sheet is provided, at least in the area intended for the passage of body fluids therethrough, with apertures for allowing such passage of body fluid. The open area of the apertures comprise from 1.3% to 35% of the total area intended for the passage of body fluids.

It has been discovered that by this unique selection of heavily titanium dioxide loaded polyolefin sheet material, coupled with the prescribed limited range of open area, which selection manifests itself in a facing sheet having the prescribed minimum brightness level, the defined facing material not only functions so as to be clean and dry but is also perceived by the user as clean and dry and hence provides the user with the desired mental comfort. Heretofore, it has been suggested that apertured polyolefin sheets may be employed as facing, and in U.S. Pat. No. 4,135,021 for example, such sheets have employed minimal levels of titanium dioxide to delusterize the polyolefin and give the sheet a white appearance. It has been found that such quantities as have been suggested are totally inadequate to preclude the appearance of stain when used in conjunction with body fluid absorbing products.

It has also been suggested that apertured polyolefin films be employed wherein the open area i.e., area of openings of the apertures as a percent of total area, may vary over a wide range. Instead, it has been discovered that when the lower end of this prior suggested range of open area is employed, even if adequate to provide the function of rendering the film pervious, the appearance of stain still is manifested in the finished product in that the closed area is at least sufficiently transparent to expose the underlying stained absorbent. On the other hand, when a large degree of open area is employed, the stain becomes visible through the apertures themselves and as a result is again apparent to the user.

In contrast to the teachings of these prior suggestions, it has been discovered that by selecting a facing material having a high level of titanium dioxide and a narrow range of open area, the visibility of the underlying stain is greatly reduced. This reduced visibility correlates with the brightness of the facing material. The term "brightness" as used herein quantitatively is defined by the test procedure set out hereinafter but may be understood conceptually to mean the quantity of light reflected by the test sample, expressed as a percentage of the light reflected from a standard sample, when both are measured by identical techniques under the same conditions of illumination. The higher this percentage, the greater the masking abilities of the facing material. It has been discovered that significant masking occurs when the facing material has a brightness of at least about 45%.

BRIEF DESCRIPTION OF THE DRAWINGS

FIG. 1 is a perspective view of a first sanitary napkin incorporating the facing of this invention, shown with parts removed;

FIG. 2 is a transverse, cross-sectional view of the napkin of FIG. 1, taken through line 2—2;

FIG. 3 is a longitudinal, cross-sectional view of the napkin of FIG. 1, taken through line 3—3;

FIG. 7 is a graphical representation of the relationship between brightness, open area and loading levels of titanium dioxide.

DETAILED DESCRIPTION OF THE INVENTION

Figure 4:
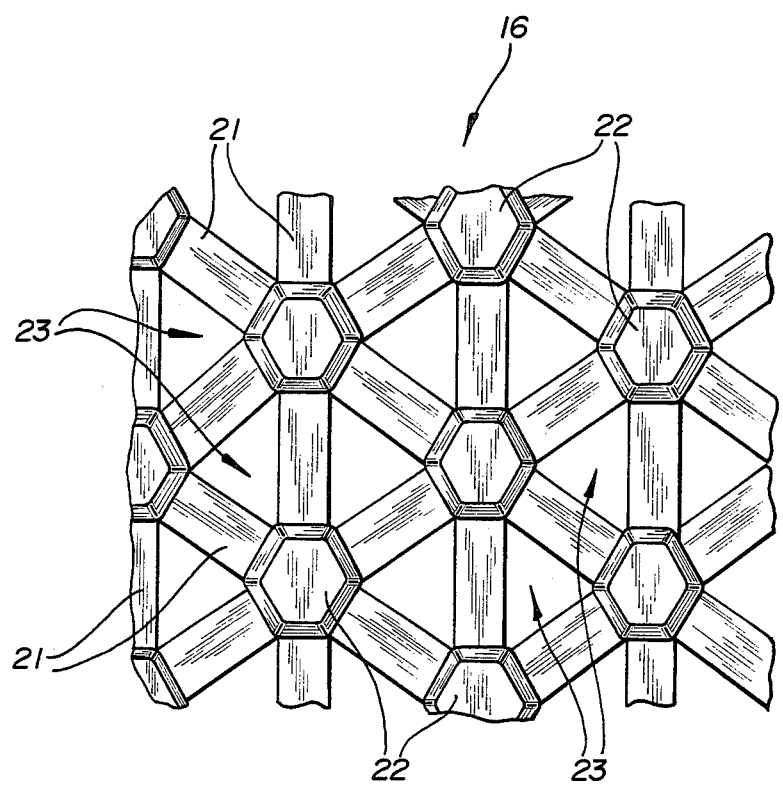
FIG. 4 is an enlarged planar view of a portion of an embodiment of the facing of this invention.

Referring now to FIG. 1, illustrated there, in perspective view is a first sanitary napkin 10, incorporating the facing of this invention. FIGS. 2 and 3 illustrate the napkin 10 in transverse and longitudinal sections respectively.

The napkin 10 consists of a generally planar pad 12 of absorbent material which may be any such material suitable for use in sanitary napkins and may include, for example, loosely associated absorbent material such as cellulose fibers e.g., wood pulp, regenerated cellulose or cotton fibers. Such fibers may be chemically or physically modified and the pad may include such fibers in combination with other materials, both natural and synthetic, such as hydrophilic foams, hydrophilic polymers or the like.

The pad 12, as illustrated in FIGS. 1-3, is wrapped in a tissue wrap 14 which is provided to aid in holding the product together during manufacturing and to help retain the shape of the finished product.

Overlying the first major surface 17 of the pad (the side worn away from the body of the user) and at least a part of the edges 19 of the pad 12, is a body fluid impervious layer 18. The layer 18 is provided to preclude body fluid from passing onto an undergarment and may be constructed of any material suitable for this purpose. For example, the layer 18 may be a polymeric film such as polyethylene, polypropylene or cellophane or may be a normally fluid pervious material that has been treated to be impervious such as a fluid repellant paper or tissue. Advantageously, the layer 18 is a heat bondable material such as polyethylene which can be bonded to the facing of this invention, layer 16, to completely enclose pad 12.

In a preferred configuration, layer 20, a nonwoven fabric, constitutes the outer layer of the garment side of the napkin 10. This fabric outer layer is provided for aesthetic purposes and for its soft feel.

As best viewed in FIGS. 2 and 3, the garment surface of the napkin 10 is provided with pressure sensitive adhesive elements 22 for adhering the napkin to the crotch portion of the wearer's undergarment. As shown in this specific embodiment, these adhesive elements 22 are in the form of three, longitudinally extending bands.

The adhesive areas or bands are protected by a release strip 24 to avoid undesired adhesion prior to use.

In accordance with the teachings of this invention, overlying the second major surface 15 of the napkin i.e. the side of the napkin to be worn against the body of the user, is the facing of this invention, layer 16.

Layer 16 is a continuous sheet comprising a polyolefin and provided with apertures for allowing the passage of body fluids therethrough to reach and be held by the absorbent core e.g., pad 12. The art is now replete with teachings for preparing apertured sheets, such methods generally requiring first forming a nonapertured continuous film of the polyolefin and then aperturing the same by means of piercing e.g. with needles or the like; embossing, followed by piercing; applying heat to weakened areas; stretching or otherwise deforming a selectively weakened film to open appertures in selected areas.

One particularly useful method is described in U.S. Pat. No. 3,137,746. Such method is generally described as the making of a net-like product by a process involving stretching a profiled polymer sheet i.e. an embossed or debossed sheet.

FIG. 4 illustrates, in enlarged planar view, a portion of such a net-like sheet material which may be employed as layer 16. Such net-like material comprises rib-like strands 21 and land areas 22 defining aperture 23.

The polymeric olefin employed in the facing material of this invention may be selected from the group consisting of polyethylene, polypropylene or copolymers thereof with the polyolefin of choice being high density polyethylene. Other polymers may be employed to enhance desired properties. For example, a particularly useful blend includes minor portions of a polymer containing an aryl group such as high impact polystyrene. Such a blend is described in U.S. Pat. No. 4,135,021. As taught therein, the aryl group containing polymer may be present in such proportion as not more than 40% by weight and preferably not more than 20% by weight, e.g., 5–20% by weight.

In the aforementioned U.S. Pat. No. 4,135,021 it is taught that the material can contain up to 5% by weight of an inert delustering filler such as titanium dioxide, said to improve the appearance and splittability characteristics of the material. In contrast to this teaching it has now been discovered that such a material is wholly inadequate to mask the underlying stain on the surface of the absorbent area of a body fluid absorbing product and hence will not accomplish the objectives of this invention. Instead, it has been discovered that the facing material of such a product, in order for it to meet such objectives must, in conjunction with the prescribed open area limitations set out herein, be heavily loaded with titanium dioxide (or with a material having the equivalent opacifying properties). Such loading must be greater than 5% by weight although preferably less than 12% by weight. The upper limit of such loading is selected by the fact that beyond 12% by weight, titanium dioxide tends to separate out of the polymer mix during manufacture and hence higher loadings are impractical. Preferably, such loading should vary from about 7% to about 10% by weight.

As set out herein, to achieve the desirable masking effect, the high titanium dioxide loading must be coupled with a prescribed limited range of open area. As used herein open area is the total area of the apertures in the facing expressed as a percentage of the total area of the facing, as measured on the body facing side of the absorbent product. Clearly no open area at all will maximize the ability of the facing to mask the underlying stain at a given level of titanium dioxide content. Needless to say, no open area will likewise preclude passage of body fluid into the absorbent area of the product and hence some open area must be provided. In U.S. Pat. No. 4,324,246, it is taught that such open area should be at least 35% and preferably at least 55%. It has now been discovered that if such large open area is employed, the masking effect of the facing is greatly reduced, irrespective of the titanium dioxide loading, in that the underlying stain is clearly visible through the facing. Further, it has been discovered that such large open area is entirely unnecessary to obtain satisfactory transmission of the body fluid through the facing and into the core. Open areas of from about 15% to about 35% are wholly adequate to meet the body liquid transmission requirements of such products as full sized sanitary napkins and, in the case of products designed to meet low body liquid flow rates, such as mini pads, panty shields and the like, open areas as low as 1.3% are acceptable. It should be understood that such low open area facing materials, per se, while capable of meeting liquid transmission rates required for body fluid absorbent products, would still not meet the objectives of this invention i.e., the masking of the underlying stain, without also meeting the herein prescribed limitations with respect to opacity e.g., a high loading of titanium dioxide.

Referring again to FIGS. 1–3, the napkin 10 is illustrated after having a quantity of body fluid applied thereto. As is schematically illustrated in these figures, the underlying pad 12 and the tissue wrapper 14 all exhibit a dark hued stain 26. As viewed in FIGS. 2 and 3 it can be seen that because of the hydrophobic, non-wetting characteristics of the prescribed facing material of the layer 16, the body fluid does not actually reside to any substantial degree on or in the layer 16. This notwithstanding, prior facing materials have allowed the stain to be visible through facing. In contrast thereto, by following the teachings of this invention, the visibility of the underlying stain is greatly diminished and, as is illustrated in FIG. 1, only a faint indication of the stain, in area 28, is visible.

Figure 5:
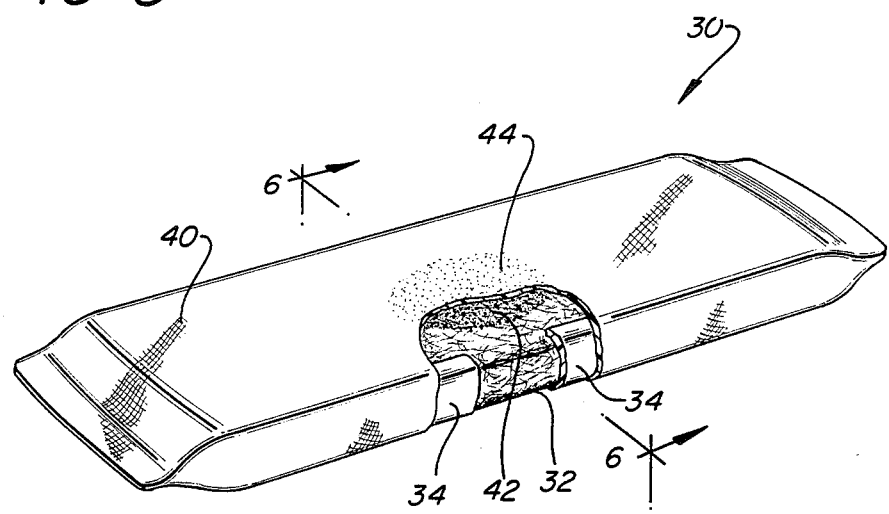
FIG. 5 is a perspective view of a second sanitary napkin incorporating the facing of this invention; again shown with parts removed.
Figure 6:
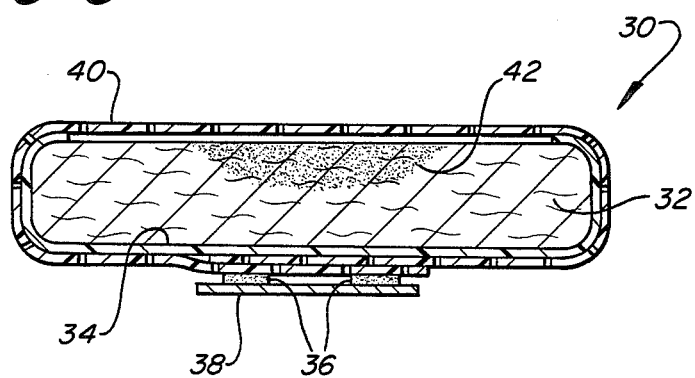
FIG. 6 is a transverse, cross-sectional view of the napkin of FIG. 5 taken along line 6—6.

Referring now to FIGS. 5 and 6, illustrated therein is another embodiment of this invention employing the facing material in an alternative sanitary napkin 30. The napkin 30 is provided with an absorbent core, pad 32. Overlying the garment facing side of the napkin is a barrier layer 34 which also overlies the longitudinal edges and, as is illustrated, may overlie a portion of the body facing side. In a manner similar to the napkin shown in FIGS. 1–3 napkin 30 is provided with adhesive elements (two) 36 for adhering the napkin to an undergarment, said adhesive elements being protected, prior to use, by a release strip 38.

A sheet of facing material 40 is provided, overlying the body facing portion of the napkin and overlapping on the opposite, garment facing side, thereby completely enveloping pad 32 and barrier layer 34. This sheet, in accordance with the teachings of this invention and at least for those portions which overlie the body facing side of the napkin, conforms to the prescription herein with respect to materials of construction, open area and titanium dioxide loading.

As is illustrated best in FIG. 5, the stain pattern 42 is clearly visible on the pad 32 but is only faintly visible through the facing 40 in the area 44.

The advantages of this invention will be better understood by consideration of the following examples.

EXAMPLE 1

A series of apertured film sheet material having various degrees of opacity and open area are tested for brightness.

The brightness test employs a Carl Zeiss photoelectric reflectance photometer Model No. 85364 whose components and mode of operation are described in "Operating Instructions Photoelectric Reflectance Photometer ELREPHO" published by Zeiss to accompany the instrument and incorporated herein by reference. Basically, the brightness measured by this instrument is defined in terms of directional reflectance of a sample which is quantified as the ratio of 457 mmu (blue-white) light reflected by the sample as compared to that reflected from an ideal mat white reference surface under equal conditions of illumination. The instrument indirectly illuminates a sample and a reference surface using two filament lamps. Images of the sample and the calibrated reference are cast on photocells. Differences in the currents flowing through these photocells are indicated on a null detector. Varying radiant flux in the reference beam through a mechanical diaphragm balances the unit and permits the directional reflectance of the sample to be read directly. The instrument is first calibrated by turning the filter changer to position 12 (which is a blank obscuring the photocells and both light beam paths). The instrument is zeroed by adjusting the indicator pointer to zero using zero point adjustment knob. Next the filter is set to position 8 (which utilizes the R457 filter). The stage of the instrument is removed and replaced with the opal glass standard (No. 21858). The graduated drum is rotated through 82.85 percent. The fine adjustment is used to check zero, and if not zeroed, is zeroed by use of the neutral wedge control. With the swing arm in position, the graduated drum is set to read 93.7 percent. The glass standard is removed, replaced with the stage and the swing arm is placed in the out position. A sample of the cover material being tested is placed on the black stage to completely cover the stage. Using the fine adjustment while rotating the graduate drum, the needle is brought to the zero position. Once the needle is zeroed the percent brightness is read directly from the graduated drum.

A series of wood pulp pads weighing 6 gms and having the overall dimensions of 10.2 cm long by 7.6 cm wide and 1.8 cm thick, have fifteen milliliters of an ersatz menstrual fluid applied to a central position in the top surface thereof. The ersatz menstrual fluid is a liquid having the salt content and surface tension characteristics of menstrual fluid and is colored to resemble the same and stain the pad.

Each of the series of apertured film materials is placed over a stained pad and a panel of ten people is asked to rank each of the various apertured film materials in order of the greatest masking ability. The results are tabulated below:

TABLE 1

| | CORRELATION OF BRIGHTNESS WITH MASKING ABILITY | | | |
|---|---|---|---|---|
| Sample | Open Area (%) | TiO$_2$ (wt %) | Brightness | Results |
| 1 | 27.4 | 7.5 | 52.4 | 10 of 10 rated best |
| 2 | 35.4 | 5.0 | 47.0 | 10 of 10 rated 2nd best |
| 3 | 43.3 | 3.8 | 36.1 | 7 of 10 rated 3rd |

TABLE 1-continued

CORRELATION OF BRIGHTNESS WITH MASKING ABILITY

| Sample | Open Area (%) | TiO$_2$ (wt %) | Brightness | Results |
|---|---|---|---|---|
| 4 | 48.0 | 1.5 | 31.4 | best 7 of 10 rated 4th best |

As can be seen from the above Table 1, there is an excellent correlation between the quantitatively determined parameter, brightness, and the subjectively perceived masking ability of the cover material.

EXAMPLE 2

A series of apertured film materials are prepared having various open areas and various titanium dioxide contents. Each of the films were about 1 mil thick and were predominantly comprised of polyethylene. Additionally, an apertured film sample, 2 mil thick and having an open area of 58.5% was prepared. The samples were tested for brightness, in accordance with the test described in connection with Example 1. The results are reported in Table 2 below and in FIG. 8 graphically.

TABLE 2

BRIGHTNESS AS A FUNCTION OF TiO$_2$ CONTENT AND OPEN AREA

| SAMPLE | TiO$_2$ (WT %) | OPEN AREA (%) | BRIGHTNESS |
|---|---|---|---|
| 1 | 7.5 | 22 | 58 |
| 2 | 7.5 | 27.5 | 53 |
| 3 | 10.0 | 35.5 | 49.5 |
| 4 | 5.0 | 25 | 51.5 |
| 5 | 5.0 | 27 | 51 |
| 6 | 5.0 | 35 | 48.5 |
| 7 | 3.0 | 43 | 41.5 |
| 8 | 1.5 | 33.5 | 42.5 |
| 9 | 1.5 | 34.5 | 42.5 |
| 10 | 1.5 | 37.5 | 40 |
| 11 | 1.5 | 43 | 39 |
| 12 | 1.5 | 48 | 34.5 |
| 13 | 0.0 | 33.5 | 17 |
| 14 | 7.8 | 58.5 | 35 |

As can best be seen in FIG. 8, the values having high brightness, i.e., above a brightness value of about 45 and preferably above about 47, are all clustered in the area of low open area and high titanium dioxide concentration. Satisfactory brightness is realized when the open area is less than about 35% and preferably less than about 30% when coupled with titanium dioxide concentration of more than about 5% and preferably more than about 7%.

We claim:

1. In a product to be worn for absorbing body fluids and comprising an absorbent core having a body facing side and a garment facing side, the improvement wherein said body facing side has an overlying facing layer comprising a continuous sheet comprising a polyolefin selected from the group consisting of polyethylene, polypropylene or copolymers thereof; said sheet having apertures therethrough for allowing for the passage of body fluids; said sheet comprising from about 5 to about 12% by weight of a opacifying agent; said apertures comprising at least about 15% open area but an amount of open area insufficient to reduce the brightness of the film to less than 45.

2. The product of claim 1 wherein the sheet comprises an open area in an amount insufficient to reduce the brightness of the film to less than about 48.

3. The product of claim 1 wherein the sheet comprises as the opacifying agent titanium dioxide.

4. The product of claim 1 wherein said sheet is a net-like material comprising land areas connected by rib-like strands, said land areas and said rib-like strands defining therebetween said apertures.

5. The product of claim 1 as a sanitary napkin.

6. The product of claim 1 as a disposable diaper.

7. The product of claim 1 as a wound dressing.

* * * * *